United States Patent
Hageman

(10) Patent No.: US 9,427,011 B2
(45) Date of Patent: Aug. 30, 2016

(54) NON-ALLERGENIC INGREDIENTS AND FOOD PRODUCTS

(75) Inventor: Robert Johan Joseph Hageman, Wageningen (NL)

(73) Assignee: N.V. Nutricia (NL)

( * ) Notice: Subject to any disclaimer, the term of this patent is extended or adjusted under 35 U.S.C. 154(b) by 792 days.

(21) Appl. No.: 12/364,717

(22) Filed: Feb. 3, 2009

(65) Prior Publication Data

US 2009/0181154 A1    Jul. 16, 2009

Related U.S. Application Data

(63) Continuation of application No. PCT/NL2007/050393, filed on Aug. 3, 2007.

(60) Provisional application No. 60/821,461, filed on Aug. 4, 2006.

(51) Int. Cl.

| | |
|---|---|
| *A23L 1/30* | (2006.01) |
| *A23D 9/013* | (2006.01) |
| *A23L 1/29* | (2006.01) |
| *A23L 1/305* | (2006.01) |
| *A23L 1/308* | (2006.01) |
| *C11C 1/04* | (2006.01) |
| *A61K 45/06* | (2006.01) |

(52) U.S. Cl.
CPC ............. *A23L 1/3014* (2013.01); *A23D 9/013* (2013.01); *A23L 1/296* (2013.01); *A23L 1/3008* (2013.01); *A23L 1/308* (2013.01); *A23L 1/3053* (2013.01); *A61K 45/06* (2013.01); *C11C 1/045* (2013.01); *A23V 2002/00* (2013.01)

(58) Field of Classification Search
CPC .................. A61K 31/715; A01N 43/04
See application file for complete search history.

(56) References Cited

U.S. PATENT DOCUMENTS

| | | | |
|---|---|---|---|
| 4,293,571 A | 10/1981 | Olofsson et al. | |
| 6,245,803 B1 | 6/2001 | Acosta et al. | |
| 6,436,464 B1 | 8/2002 | Euber | |
| 2002/0037357 A1* | 3/2002 | Fritsche et al. | 426/656 |
| 2002/0106436 A1 | 8/2002 | Gohman et al. | |
| 2007/0104761 A1* | 5/2007 | Williams | 424/439 |

FOREIGN PATENT DOCUMENTS

| | | |
|---|---|---|
| CN | 200780036351.6 | 3/2014 |
| WO | 2005/122790 A1 | 12/2005 |
| WO | WO 2005122790 A1 * | 12/2005 |

OTHER PUBLICATIONS

PCT/NL2007/050393—written opinion of the International Search Authority (PCT-237) from WO 2008/016306, published Feb. 7, 2008.*
Siemensma et al., (Trends in Food Science & Technology. Jan. 1993;4:6-11).*
IUPAC Compendium of Chemical Terminology, 1997 (1996, 68, 2291).*
Mallee et al., (AgriFood. Mar./Apr. 2007. Anno 18—No. 2 (2 pages)).*
Sawatzki, G., Georgi, G., and Kohn, G. Pitfalls in the design and manufacture of infant formulae, Acta Paediatr Suppl 402: 40-5, 1994.
Galant, Stanley P., M.D., Franz, Michael L., M.D., Walker, Patricia, R.D., Wells, Ian D. and Lundak, Robert L., Ph.D. A potential diagnostic method for food allergy: clinical application and immunogenicity evaluation of an elemental diet. The American Journal of Clinical Nutrition 30: Apr. 1977, pp. 512-516.
Hefle, Susan L. Impact of Processing on Food Allergens. Adv Exp Med Biol. 1999;459:107-19.
Geetha, P., John, Jenny Ann, and Rao, K. Jayaraj. Food Allergy—Causes and Remedies. Indian Food Industry, May-Jun. 2006, vol. 25, No. 3, 59-65.
Siemensma, Andre D., Weijer, Wicher J., and Bak, Henk J. The Importance of peptide lengths in hypoallergenic infant formulae. Trends in Food Science & Technology, Jan. 1993, vol. 4: 16-21.
Mallee, et al., "Whey Protein Concentrates From Acidic Whey: Benefits for Use in Infant Formulas," AgroFOOD Industry, Anno 18, No. 2, Mar./Apr. 2007.
IUPAC Compendium of Chemical Terminology, 1997 (1996, 68, 2291), definition of "degree of polymerization".
Office Action issued for corresponding European Patent Application No. 07808526.3, dated Nov. 6, 2012.
Office Action issued for corresponding European Patent Application No. 07808526.3 , dated Sep. 17, 2014.
B. Niggemann et al.: "Prospective, controlled, multi-center study on the effect of an amino-acid-based formula in infants with cow's milk allergy/intolerance and atopic dermatitis", Pediatr. Allergy Immunol., Jan. 1, 2001, pp. 78-82.

* cited by examiner

*Primary Examiner* — Cherie M Stanfield
(74) *Attorney, Agent, or Firm* — Banner & Witcoff, Ltd.

(57) ABSTRACT

The present invention relates to a non-allergenic food product, comprising an amino acid fraction comprising at least one component selected from the group consisting of amino acids and peptides having a degree of polymerization of 7 or less; and a lipid fraction comprising at least one fatty acid selected from the group consisting of arachidonic acid and docosahexanoic acid, the composition having a content of proteins and other peptides having a molecular weight of 1000 dalton or more of less than 0.01 wt. %, based on the dry weight, preferably less than 0.001 wt. %, more preferably less than 0.0001 wt %.

17 Claims, No Drawings

NON-ALLERGENIC INGREDIENTS AND FOOD PRODUCTS

RELATED APPLICATIONS

This application is a continuation of PCT application no. PCT/NL2007/050393, designating the United States and filed Aug. 3, 2007; which claims the benefit of the filing date of U.S. provisional application No. 60/821,461, filed Aug. 4, 2006; each of which is hereby incorporated herein by reference in its entirety for all purposes.

FIELD

The present invention relates to a food product that is easily digestible, a non-allergenic food product, a method of preparing such product, a method for treating an allergic person, a method for diagnosing a food allergy in an allergic person and to a composition suitable as an ingredient for a food product according to the invention.

BACKGROUND

Food allergy is a common and growing problem. It may manifest itself early in life. Infants. In particular those having a so-called atopic constitution, may develop an allergic reaction to various proteins, like those originating from cow's milk, soybeans, egg, peanuts or wheat (gluten). Usually these allergies disappear after several months to years. Later in life new allergies may develop, such as those from dust mites, pollen or other proteins from flowers or constituents from fruit.

People suffering from an allergy may have difficulties in digesting or metabolizing some food constituents, which may lead to undesired side effects and intolerance to such constituent. Lactose-intolerance is a commonly known example thereof, which for that reason is often excluded from hypo-allergic nutritional formulae.

Allergic persons may develop gastrointestinal problems if such a constituent is present in their diet, which may further aggravate the condition of the person.

In allergic persons a strong systemic reaction typically develops after exposure to the allergen. This may result in a variety of symptoms, immediately after exposure, and later, for instance after 1 or 2 days, These reactions are thought to be mediated by the interaction of allergens with Langerhans type cells or dendritic cells, regulatory T cells and with Toll-like receptors (TLR) for example the TLR-4 in cells of the Gut-Associated Lymphoid Tissue (GALT). Through activation of a variety of lymphocytes, eosinophylic cells, mast cells and basophilic cells a specific release of immunoglobulins (Ig), proteases, histamine and cytokines, prostaglandines (PG), leukotrienes, hydroxy eicosatetraenoic acids, interleukins (IL) and other signalling compounds a response is generated to the allergen. It is contemplated that in particular the IgE release by B-cells plays an important role. The constitution of a person to develop an allergic reaction appears to be related to the number of T-helper cells of type 1 and 2 and the amount of regulatory T cells. In particular a low ratio of the number of Th1 to that of Th2 cells, and an abnormal value in the GALT of the ratio of the number of Th2 to that of regulatory cells is thought to reflect an increased risk to developing an allergic reaction. Typically in healthy non-allergic infants such ratio is relatively low briefly after birth, and increases rapidly in the first weeks thereafter.

Symptoms that may be observed as a result of an allergic reaction include a reaction of the skin (irritation, local inflammation), a reaction of the mucus-generating tissue like that in nose, mouth, gut-epithelium, lung and throat (allergic rhinitis, irritation, sneezing, swelling), of the eyes (tears), of the respiratory system (asthma, ventilatory obstruction), of the gastrointestinal tract (diarrhoea, inflammatory response locally or over longer distances of the gut), a systemic reaction (as e.g. manifests itself in increased plasma levels of histamine and lower levels if interferon-gamma) and behavioral problems (irritability, crying periods of babies).

An atopic skin reaction of young infants also frequently leads to an inflammatory response at the child's bottom (diaper rash). Inflammation may also develop in allergic adults, e.g. if they scratch itching areas too many times.

The allergic reactions may further cause pain, itching feelings, and a decrease in performance and body condition. In persons suffering from allergic asthma or allergic bronchitis a shortness of breath is caused. Further it may hinder the sleeping pattern or prevent a normal functioning in life. It may even cause problems that have a severe clinical impact such as causing a shock, in particular an anaphylactic shock.

An anaphylactic shock or another form of an anaphylactic reaction may also occur when insufficiently pure drugs are applied in the treatment of a person having an atopic or allergic constitution, and in particular when the drug is administered via the parenteral route. Examples of such drugs which are known to be at risk for pollution with traces of allergens are antibiotics, local anaesthetics, codeine, drugs prepared from animals or by using exogenous proteins like enzymes such as insulin, adrenocorticotropic hormone, enzymes as such, diagnostic agents like contrast media for MRI or X-ray, vaccines, antitoxins, gamma globulin, interferons, etc. Such anaphylactic shock may further occur when a person, who is at risk for developing such an allergic reaction, is exposed to a venom of plants or animals, for instance that of insects, such as bees, wasps or hornets.

Diagnosis of food allergy is a cumbersome task, especially in young infants. Because classical allergy skin tests are considered to be rather aggressive to babies, other methods are frequently applied such as trial and error experimentation, using conventional diet ingredients, or using less allergic synthetic foods ("hypo-allergic" foods). The potential occurrence of delayed reactions makes interpretation of the results troublesome. Moreover hypo-allergic food may still cause an allergenic reaction. Food legislation defines the criteria to which a hypoallergenic formula must comply. Herein a food is considered hypo-allergenic if its allergenicity is at least 1000 times lower in a challenge test in guinea pigs than the original material from which the ingredients have been prepared.

An example of such a hypo-allergenic food product is Neocate. It comprises amino acids (inter alia tryptophan, threonine, arginine and methionine). The product does not comprise fibers, nor long chain polyunsaturated fatty acids (abbreviated as LCP's).

A need exists for a food product that is non-allergenic, in particular a food for infants, more in particular a food for infants having an atopic constitution.

It would be desirable to provide a non-allergenic food product that provides satisfactory nourishment to the subject, meeting all nutritional demands of such subject, and which product is palatable, and/or convenient to use.

Further, it would be desirable to provide a food that is suitable for use in a diagnostic method for determining an allergy.

It would also be desirable to provide a food product that is capable of ameliorating an allergic response of a subject that is exposed to (small amounts of allergens), e.g. when nourished with a food product that comprises small amounts of allergens or when exposed to drugs that might comprise traces of allergens.

In the gastrointestinal tract of specific groups of infants several conditions prevail, which increase the sensitivity to allergens and favor intolerance to food components. For example infants of young gestational age frequently suffer from an underdeveloped capacity to digest food components, and release abnormal quantities of gastrointestinal hormones and enzymes. This imparts immune function, and in particular the reaction to potential allergens. Coeliac patients suffer from an incapability to completely digest gluten proteins and peptides. Persons suffering from short bowel syndrome and diarrhoea experience increased transit times, which do not allow proper digestion and absorption of the digestive components. Persons suffering from inflammation of the epithelial cells in the gastrointestinal tract such as those suffering from Crohn's disease and other inflammatory bowel diseases, and persons experiencing long-period use of drugs like non-steroidal anti-inflammatory agents, experience a decreased capacity for digestion and absorption of food components.

Also patients, in particular infants, that are exposed to treatment of specific groups of medicaments, such as antibiotics or chemotherapeutics, develop an increased sensitivity to generate an allergic reaction to exposure to a potential allergen. Patients suffering from cystic fibrosis also demonstrate increased levels of larger peptides over a long distance in the gut, a deviating pattern of release of hormones and enzymes that are generated by the gastrointestinal tract and an increased risk for developing allergy.

Despite great efforts to properly feed these specific groups of subjects, especially children, many of them become malnourished. The diseased state of these specific groups also mandates taking all possible precautions to avoid the development of an allergic reaction to the food product that is administered. Therefore a need exists for a food product that properly nourishes specific groups of malnourished persons or diseased persons and that at the same time prevents the development in these patients of an allergic reaction after exposure to potential allergens.

SUMMARY

It is an object of the invention to provide a novel food product, in particular a non-allergic food product that meets one or more of the needs, desires and/or effects identified in the present specification and/or claims.

It has now been possible to meet such object by providing a food product having a specific amino acid fraction, a specific lipid fraction and optionally a specific carbohydrate fraction.

Accordingly, the present invention relates to a food product comprising
  an amino acid fraction comprising at least one component selected from the group consisting of free amino acids, including salts thereof, and peptides having a degree of polymerization of 7 or less;
  a lipid fraction comprising at least one lipid selected from the group consisting of arachidonic acid (AA) and docosahexaenoic acid (DHA); and optionally
  a non-digestible carbohydrate fraction comprising at least 80 wt. %, based on the weight of the carbohydrate fraction, of oligosaccharides having a degree of polymerization in the range of 3-20, the composition having a content of peptide material (amino acids and peptides, including proteins) having a molecular weight of 1000 Dalton or more of less than 0.01 wt. %, based on the dry weight, preferably less than 0.001 wt. %, more preferably less than 0.0001 wt % and most preferably less than 0.00001 wt %, or even below the detection level, or fully absent.

DETAILED DESCRIPTION OF CERTAIN PREFERRED EMBODIMENTS

Embodiments of the invention are directed to food products characterized as being basically non-allergenic.

The term "non-allergenic" is defined herein as having a content of peptide material having a molecular weight of 1000 Dalton or more of less than 0.01 wt. %, in particular of less than 0.001 wt. %, more in particular less than 0.0001 wt %, and even more in particular less than 0.00001 wt %, or even below the detection level, or fully absent.

A "ready to use" liquid product may suitably be prepared from, e.g. 25 g solid product of the invention per 100 ml of a suitable liquid, such as water, although in practice a different solid to liquid ratio may be used. When referred herein to a concentration of a component of a product in terms of weight per volume unit or moles per volume unit, generally the concentration in a "ready to use" liquid product of the invention is meant. Typically, such mentioned concentration is based on the concentration of a product having a dry weight of 25 g/100 ml. So in general, the concentrations based on dry weight are four times the mentioned concentration in weight per 100 ml, unless specified otherwise.

Preferably, the non-allergenic food product of the invention has a T-cell epitope content of less than 0.01 wt. %, based on dry weight, more preferably of less than 0.001 wt. %.

The molecular weight of peptide material can be read from the label of a commercially available food ingredient, if local legislation mandates explicitory disclosure of the detailed nature of the ingredients or preferably be determined by isolation of the peptide material and subsequent analyses of its molecular size. Isolation can be done by purification and separation from the other constituents that are present in the nutritional product, based on methods known in the art such as extraction, filtration and chromatography. Quantification is possible by separation, by chromatographic or electrophoretic techniques and subsequent analysis, e.g. by spectroscopic methods.

The non-allergenic character of the food product of the invention also allows the use of the food as (complete) nourishment to allergic humans, in particular infants (age 7 or younger), or even babies.

The food product is also suitable for use as nourishment to a human, including infants, in particular babies, during a period wherein the subject is tested for an allergy. It is advantageous that the food product of the invention can be used without a substantial risk to interfere with said test, in that it can be used without a substantial risk to give an allergenic reaction due to a constituent in the food product.

The inventors further contemplate that the food product of the invention may actually reduce an allergic reaction to allergens that are not present in the food. Without being bound by theory, it is hypothesized that the food product may have a positive effect on the ratio Th1/Th2 and the amount of IgE that is released after exposure to an amount of a specific allergen, due to the presence of the specific non-allergic lipid (AA and/or DHA) and optionally the specific non-allergic non-digestible carbohydrate fraction.

Usually, the amino acid fraction, the lipid fraction and the carbohydrate fraction are present in an amount such that the amino acid fraction provides about 8 to about 15.7 energy %, the lipid fraction provides about 38 to about 52 energy % and the carbohydrate provides about 38 to about 47 energy %. These amounts are based on the following energy contributions: 16.8 kJ/g for proteins, peptides, amino acids, organic acids and digestible carbohydrates and 37.8 kJ per g lipid. No energy is attributed to other components such as fibers (indigestible carbohydrates), minerals, vitamins and nucleotides or equivalents thereof.

The energy density of the ready to use nutritional products according the invention is between about 2.52 to about 3.24, and preferably between about 2.6 and about 3.1 kilojoule per milliliter (or between about 10.04 and about 12.96 kilojoule per 100 g dry weight, respectively between about 10.4 and about 12.4 kilojoule per 100 g dry weight), in particular to make it especially suitable for administration to an allergic infant.

The amino acid fraction is the total of amino acids in free form (including salts and esters thereof), and amino acids present in the form of peptides (including proteins, glycoproteins and lipoproteins). It provides a source of amino acids from which the body can synthesize proteins and other peptides. Usually the amount of peptides (including proteins) having a degree of polymerization (DP) of 8 or more is less than 0.01 wt. %, based on the total dry weight of the product. In view of the non-allergenic character of the product it is preferred that the amount of peptides having a DP of 8 or more is less than 0.001 wt. %.

Preferably arginine is present. Best results are obtained by using an amino acid fraction, which contains about 1.0 to about 7.1 gram arginine per 100 gram amino acids. However, preferably the arginine content is relatively low, in particular in the range of about 1.0 to about 6.9 gram or even better about 1.5 to about 6.0 gram arginine per 100 g of the amino acid fraction, in order to ameliorate an allergic reaction.

Preferably threonine is present, because threonine may increases mucin production in gut which decreases exposure to allergens of epithelial cells, allows better digestion of food allergens and increases removal of allergens. Threonine is in particular considered effective with respect to a relatively slow reaction to food allergens, that have been consumed. The threonine content can be about 5.0 to about 13, but is preferably in the range of about 5.5 to about 11 gram threonine per 100 g of the amino acid fraction.

Preferably tryptophan is present, because it may increase the Th1/Th2 ratio, or it may decrease the Th2/regulatory T cells ratio, which effects decreases the reaction to a potential allergen. It may be effective with respect to the immediate— or the delayed reaction after exposure, or to both types of reactions. The tryptophan content is in the range of about 2.0 to about 7.0, but preferably about 2.2 to about 6.0 gram tryptophan per 100 g of the amino acid fraction.

Preferably asparagine and/or aspartic acid are included to support the immune system, in a concentration of about 6.4 to about 15, preferably about 8 to about 13, more preferably about 9 to about 12 gram aspartic acid equivalents (sum of asparagine and aspartic acid) per 100 gram amino acids.

The amino acid fraction preferably comprises all essential amino acids.

A food product intended for PKU patients is typically free of phenylalanine.

The lipid fraction is the total of lipids in the product. In particular, the lipid fraction may comprise at least one lipid, in particular at least two lipids, more in particular at least three lipids, selected from the group consisting of triglycerides, diacylglycerides, mono-acylglycerides, phospholipids, lysophospholipids, ceramides, sphingosines, gangliosides, globosides, sulfatides, steroid esters, free fatty acids, salts of free fatty acids and esters of free fatty acids. Preferably at least 80 wt. % of the lipid fraction is formed by the one or, preferably, the at least two or at least three lipids of this group.

As indicated above, the lipid fraction comprises at least one lipid selected from arachidonic acid (AA) and docosahexanoic acid (DHA). AA and/or DHA may be present as a free fatty acid, as a salt of the free fatty acid, as an ester of the free fatty acid (for instance as a glyceride ester), as an amide, or in another form acceptable for use in a food product.

The inventors have realized that a beneficial aspect of the presence of AA is its role in the prostaglandin production in the body, in particular of PgE2. The inventors contemplate that this production is beneficial to the subject nourished with the product, even though prostaglandins are commonly considered to increase the allergic response.

The inventors have come to the conclusion that DHA may contribute to a reduction in an inflammatory reaction as a result of an allergic response, in particular a local inflammatory reaction that is a secondary complication, e.g. as a result of too much scratching or as a result of diarrhea.

It is further contemplated that dietetic DHA improves the membrane composition of cells involved in the immune response. This leads to more specific recognition patterns of potential allergens and changes signalling pathways after activation of receptors, e.g., of those cytokines that are involved in an allergic reaction and thus changes the reactions to an exposure to a potential allergen.

It is further contemplated that the presence of AA, DHA or both may be advantageous in that these modify the way the central and/or the enteral nerve system reacts to the presence of peptidic material of foreign origin. In particular these components may dampen the reaction of the enteral nerve system to the presence of a potential food allergen in the gastrointestinal tract and in particular the reaction to antigen presenting cells. It is thought that this may be the result of a beneficial effect on the structure and functioning of the membranes of the nerve and dendritic and other cells that are involved with the immune reaction.

It is further contemplated that AA, DHA or both may contribute to reduction or avoidance of feelings of depression, which feelings may adversely influence an allergenic response.

The AA content preferably is at least 0.25 g/100 g fatty acid (including fatty acid in a bound form, such as in an ester (including glycerides), an amide or a salt). The content can be as high as about 6 g/100 g fatty acid, but preferably the concentration in the lipid fraction is in the range of about 0.4 to about 0.8 g arachidonic acid per 100 g fatty acids.

The DHA content preferably is at least 0.15 g/100 g fatty acid. The content can be as high as about 1.5 g/100 g fatty acid, but preferably the concentration is in the range of about 0.16 to about 0.8 g DHA per 100 g fatty acids.

Preferably the ratio of the weights of AA to DHA is about 1-5:1.

Preferably one or more n-3 fatty acids are included. The presence thereof is considered advantageous in order to prevent or at least reduce an accumulation of docosatetraenoic acid in the membranes of cells, in particular nerve cells and/or retina cells. Besides, DHA preferred examples of n-3 fatty acids include alpha-linolenic acid (ALA), eicosopentaenoic acid (EPA) docosapentaenoic acid (DPA3).

For preventing accumulation of docosatetraenoic acid the ratio linoleic acid (LA) to the sum of DPA and DHA and EPA can be about 10-60:1, but is preferably lower, in particular about 0-47:1 or even better about 10-40:1.

The lipid fraction does preferentially not comprise peptidic material such as e.g. the proteinaceous part of lipoproteins, having a molecular weight of 1000 Dalton or more in a concentration of more than 0.01 wt % and preferably comprises less than 0.001 wt % of such material.

The lipids according the invention can be isolated from natural material that comprises such peptidergic material, such as tissue from animal, vegetable, fungal or bacterial origin. Examples of lipids from animal origin are milk, egg or brain, or fish. Vegetable lipids are in particular those lipids isolated from seeds or pulses which comprise more than 1% DHA or AA. An example of lipids from fungal origin are those oils that are isolated from Mortierella or Pythium species or from modified yeasts.

Proteinaceous material must be removed by methods that are specific for the raw material which has been selected. Several general methods of purification of raw oils and lipids are known in the art, such as acid treatment (which also removes gums), bleaching or treatment with absorbents like silicates, filtration techniques, crystallization or cooling and deodorizing methods. These can be suitable for purification of the lipids according the invention.

However, the lipids according to the invention can meet the specification only by modifying one or more of these process steps or to apply one or more additional steps to remove or destroy residual peptidic material, which includes the lipoproteins and processing aids like enzymes. Such an additional step can for example be absorption to a chomatographic column or adapted filtration bed at elevated temperatures (>50° Celsius).

A further example of a modified method is applying micro- or ultrafiltration. Such a method can be successfully applied once a pre-filtration has occurred either by filtration via traditional methods (using large pore filters or filter aids) or by centrifugation. Suitable pore sizes for microfiltration are below 5 micrometer and preferably the pore size of the final filter is 0.01-1 μm.

Also components can be added to the non-pure lipid fraction prior to filtration or absorption, which attach to the peptidic material to increase absorption to columns. Such material may also be added to increase flocculation rates of the proteins during winterization or cooling or to increase filtration efficacy. Such components are preferably food grade materials like amphoteric materials like choline, betaine, dimethylglycine, or one or more minerals selected from the group of calcium and magnesium.

Ceramides, sphingosines, sulfatides, globosides, and other glycosidated lipids require adapted methods to isolate these more polar lipids from the peptidic material. In particular chromatographic methods like those that apply ion exchange, in particular anion exchange appear to be useful.

Synthetic materials like several di- or mono acylglycerides and lyso-phopholipids are frequently manufactured by using lipases or phospholipases. The nature of these enzymes determines the modified or additional step to be applied. For example denaturation of globular enzymes makes a thermal treatment before precipitation and filtration or centrifugation attractive. Filtration can occur in one or more steps. Preferably rough filtration or centrifugation is combined with a microfiltration step at elevated temperature.

Suitable heating temperatures for denaturating these lipases are above 80° C. and preferably from about 85° to about 110° C.

It is preferred to adapt the lipid sources in order to change micelle formation in the liquid product and in the digestive tract, and thus improve the digestion characteristics. This is achieved by including relatively low amounts of triglycerides in the product. In conventional infant formulae, which are prescribed for malnourished infants or infants that cannot consume normal volumes of liquid formulae, the triglycerides levels can amount to levels up to 7.0 g per 100 ml ready to use formula (or up 28.0 wt. % dry weight). It is preferred to apply one of the following two methods to decrease the amounts of triglycerides. The first method implies a decrease to values below 4.0 g/100 ml (or below 16.0 wt. % dry weight), preferably in the range of about 2.9 to about 3.9 g/100 ml ready to use formula (or about 11.6 to about 15.6 wt. % dry weight). Most preferably the amount of triglycerides amounts to about 3.0 to about 3.7 gram per 100 ml (or about 12.0 to about 14.8 wt. % dry weight).

In the second method, at least part of the triglycerides is replaced by one or more members of the group of alternative lipids, which consist of mono- or diglycerides, phospholipids, gangliosides, lysophospholipids, ceramides, sphingosines, modified ceramides (sulfatides, etc) and cholesteryl esters. The higher the lipid content in the formula the more triglycerides must be replaced. It was found that amounts of about 3.4 gram triglycerides can be digested properly by most infants, when the emulsion is properly made and in particular gives droplets having an average particle size [dp(3,4)] of 5 micron or less and preferably of 0.1-3 micron for reconstituted dry products and 0.1-0.3 for ready to use liquid products. It is preferred to replace the remainder of the lipid fraction, being the difference between the total lipid fraction and 3.4 g triglycerides, with alternative lipids. In particular in nutritional products having a triglycerides content of 2.9-3.9 g/100 ml ready to use formula, it is especially advantageous to include about 0.5 to about 4 wt. %, preferably about 0.7 to about 3 wt. % of the lipid fraction as phospholipids and to include about 0.4 to about 1.4 wt % cholesterol or equivalents thereof, such as cholesteryl esters. The nutritional products that comprise such alternative lipids form emulsions, which are easily digested. It is envisaged that this is in particular due to an improved proteolysis by chymotrypsin. In addition it is conceived that the products that result from the digestion differ from those of conventional formulae, and the contents of the lumen of the upper part of the gastrointestinal tract, in particular jejunum and ileum, which hold such products are, as a result, presented differently to the dendritic cells and the Toll-like receptors in the gastrointestinal tract and in particular to the TLR-4, which are present in the GALT.

This difference in presentation will also involve bacteria, bacterial products and fragments of bacterial cell walls. When the lipid comprises more than 0.1 wt % cholesterol, or equivalents thereof, it becomes beneficial to include in the formula fragments of bacterial cell walls, in particular of those bacteria that are commensals in the upper part of the digestive tract, such as Lactobacilli and Bifidobacteriae. Advantageous amounts are 10 to the power eight to 10 to the power eleven bacteria, or about 0.02-0.4 g fragment rich material per 100 ml ready to use product (or based on dry weight: 4 times 10 to the power eight to 4 times 10 to the power eleven bacteria per 100 g product, or about 0.08-1.6 wt. % fragment rich material). The latter material can contain nucleotides.

The non-digestible carbohydrate fraction is the total of non-digestible carbohydrates in the product.

Non-digestibility may be determined by applying the method of Lee et al, *J. Assoc. Off. Anal. Chem.*, 75:395-416, 1992. If a carbohydrate is digestible for 50% or more, the total mass of the carbohydrate is considered to be digestible.

It is known in the art to include non-digestible carbohydrates (dietary fiber) in food product. In the art, relatively large carbohydrates (polysaccharides) are generally considered to be desirable. The inventors have come to the conclusion that relatively small indigestible carbohydrates are surprisingly effective with respect to solving a problem underlying the invention, such as ameliorating an allergic reaction.

It is contemplated that an indigestible oligosaccharide having a DP of up to 20 in a product of the invention has a positive effect on the Th1/Th2 ratio.

Further, the inventors have realized that the presence of relatively small carbohydrates (DP up to 20) is advantageous with respect to the textural and/or handling properties of the food, in particular in case the food is to be consumed as a liquid. In solution, oligosaccharides are usually essentially non-viscous or have only a minor effect on the viscosity. In particular a solution of 2 wt % in water results in a viscosity of 100 mPa·s or less at a shear rate of 100 per sec at a temperature of 20° C. Thus, such oligosaccharides can be used in a product to provide a product with a viscosity of 100 mPa·s or less, in particular of 50 mPa·s or less, preferably 20 mPa·s or less. This is found to be advantageous with respect to ease of administration (e.g. easy to drink) and/or texture/mouthfeel of the product.

Preferably, the product comprises at least one oligosaccharide selected from the group consisting of galacto-oligosaccharides, fructo-oligosaccharides, xylo-oligosaccharides, manno-oligosaccharides, galacturonic-oligosaccharides and arabino-oligosaccharides. These oligosaccharides are classified as belonging to one group of monosaccharides (for example galactose-oligosaccharides), when more than 90% of the monosaccharides that result from hydrolyses of that oligosaccharide belong to that one type. In this document they are called uni-oligosaccharides. Mixed-type oligosaccharides comprise two or more types of monosaccharides, wherein each type contributes more than 10% of the weight of that oligosaccharide.

More preferably two or more uni-oligosaccharides are included that have different fermentation patterns in terms of the generation of butyrate, propionic acid, acetate and lactate, in terms of acidification power and in the formation of gasses like hydrogen or methane. These fermentation patterns are determined by using the microorganisms that are commensals in the first part of the gastrointestinal tract, i.e. those in mouth, throat, oesophagus, stomach, jejunum and first 25% of the ileum. Especially those that occur in the mouth and in the jejunum/ileum appear important in influencing the reaction to a potential allergen.

In practice, it appears that three or more uni-oligosaccharides are most beneficial to generate sufficient amounts of butyrate and especially lactate compared to acetate and/or support growth of the variety of these naturally occurring commensals. In particular a mixture of galacto-oligosaccharides, uronic acid-oligosaccharides and xylo-oligosaccharides is beneficial, for example a mixture of galacto-oligosaccharides, pectin hydrolysate and xylo-oligosaccharides in a ratio of 1:0.2-5:0.2-5.

A disadvantage of these mixtures of uni-oligosaccharides is that each of the ingredients would comprise low amounts of peptidergic material, such as enzymes and residual proteins that origin from the starting material such as milk proteins.

Therefore, with at least equal results, alternatively mixed-type oligosaccharides can be included, which require only one purification step to remove potentially allergic peptidergic material. In particular mixed-type oligosaccharides are suitable when at least two monosaccharides are included in an amount of more than 15, or even more preferably more than 20 wt %.

Mixed-type oligosaccharides can be synthesized by reacting selected monosaccharides with each other to obtain oligosaccharides with the chain length or chemical structure as desired, or be obtained by hydrolysis of mixed-type polysaccharides. These polysaccharides are preferably of natural origin.

Suitable mixed-type oligosaccharides can also be obtained by hydrolysis of mixtures of polysaccharides to small oligosaccharides, which are subsequently attached to each other. Examples of suitable polysaccharides are mixtures of cellulose, hemicellulose and pectin and the like, like those that occur in pea fiber or various brans (rice, corn, barley) or beet fiber. Also artificial mixtures of polysaccharides can be prepared by mixing selected amounts of suitable polysaccharides like hemicellulose, cellulose, beta-glucans, algal polysaccharides, fructans, gums (like guar or locust bean or acacia gum) and mucilages. After hydrolyses and creation of the mono and oligosaccharides as desired the reaction is stopped and the reaction products isolated and used, or subjected to a new enzymatic step wherein individual mono- or oligosaccharides are attached to each other to produce new mixed oligosaccharides. Examples of suitable enzymes for synthesizing such mixed oligosaccharides include synthases or ligases or other suitable enzymes known in the art, e.g. those of microbial origin or yeast origin.

Such mixed type oligosaccharides may also be isolated from splitting oligosaccharides from proteinaceous matter.

After preparation of the mixed-type oligosaccharides they are preferably subjected to an additional purification method to remove the peptidergic material.

The aqueous slurry is therefore subjected to chromatography or absorption techniques, preferably after heating at suitable pH and filtration or centrifugation. An example of a suitable absorption material activated coal.

Examples of suitable mixed oligosaccharides include arabinoxylans, glucomannans and galactomannans. Especially those that comprise more than 1.5 wt % of a monosaccharide, which differs from the two main monosaccharides, For example an arabinoxylan oligosaccharide, which comprises more than 5 wt % of glucuronides would be suitable for the purpose of the invention. In particular, it is advantageous to include oligosaccharides, which comprise as a third component sialic acid and/or glucosamine. In particular mixed-type oligosaccharides comprising more than 3 wt % sialic acid are preferred.

If present, it is preferred that the amount of non-digestible carbohydrates is in the range of about 0.4 to about 3 g non-digestible carbohydrate per 100 kcal as provided by the product. In a highly preferred product the content is at least 0.6 g/100 kcal It is highly preferred that the content is 2.0 g/100 kcal or less.

If present, it is preferred that at least 60 wt. % of the non-digestible carbohydrates is formed by non-digestible carbohydrates having a degree of polymerization in the range of 2-10. Such carbohydrates are in particular advantageous with respect to their non-viscous character, when dissolved in an aqueous liquid.

If present, the non-digestible carbohydrates preferably comprise at least two different monosaccharide units selected from the group consisting of galactose, fructose, uronic acids, xylose, arabinose.

Usually, a food product comprises a digestible carbohydrate fraction. The digestible carbohydrate fraction may comprise one or more digestible carbohydrates which are known in the art to be suitable for use in food products, e.g. selected from digestible polysaccharides (e.g. starch), digestible monosaccharides (e.g. glucose, fructose), and digestible disaccharides (e.g. sucrose). Though traditional formulae exclude lactose in hypo-allergic and easily digestible formulae, and already a significant positive effect can be obtained by applying the measures as given above, it is preferred to include a small amount of lactose in order to promote bacterial growth in the upper part of the gastrointestinal tract, in particular that of the commensals. In particular the amount is about 0.05 to about 1.6 g, preferably about 0.1 to about 1 g per 100 ml ready to use (liquid) product (or about 0.2 to about 6.4 g, preferably about 0.4 to about 4 g per 100 g dry weight).

Usually a food product of the invention comprises a mineral fraction. Preferably, at least one of iron and copper is present. The presence of a mineral may have a positive effect on the allergic response or contribute to amelioration or avoidance of the occurrence of a symptom thereof. For instance, it is contemplated that Cu may stimulate the activity of an enzyme capable of neutralizing radicals that cause an increase of an inflammatory reaction.

In one embodiment iron and/or copper are present in the form of an encapsulated salt. An encapsulated salt can suitably be added to a (spray dried) powder product of the invention prior to packaging, or before dissolving the powder product, prior to use.

One or more other minerals may be present, in particular one or more minerals selected from the group consisting of sodium, potassium, chloride, calcium, phosphorous (as phosphate), magnesium, zinc, manganese, iodine, molybdenum, selenium and chromium.

The buffer capacity of the product requires careful consideration in such hypo- and non-allergic food products, especially for patients that suffer from malnourishment and/or suboptimal digestion processes. In particular it is important to make it as low as possible. This is achieved by selecting a phosphorus content of about 20 to about 36 mg per 100 ml ready to use (liquid) product (about 80 to about 104 mg/100 g dry weight) and preferably about 22 to about 33 mg per 100 ml ready to use (liquid) product and/or to select a calcium level of about 30 to about 54 mg calcium per 100 ml (liquid) product (about 120 to about 216 mg per 100 g dry weight) and preferably about 40 to about 50 mg calcium per 100 ml (liquid) product.

The buffer capacity is further determined by the amount of organic acids in the product. In view thereof, the amount of citric acid less than 0.5 mg per 100 ml liquid product. (or less than 2.0 mg/100 g dry weight)

In view thereof, the amount of orotic acid usually is 5 mg or less per 100 ml (liquid) product (or 20 mg/100 g dry weight or less), and will preferably be in the range of about 0.2 to about 4 mg/100 ml.

Though it is desirable for the buffer capacity to be low, it is advantageous to include carbonate, in particular added as bicarbonate in the formula, in order to support the digestion process, in particular endocrine function. The amount of carbonate, in particular added as bicarbonate, preferably should be in the range of about 0.05 to about 0.2 g per 100 ml (or about 0.2 to about 0.8 g/100 g dry weight).

It is further important that the osmolarity of the ready to use liquid product is sufficiently low to allow easy transfer through the stomach and prevention of regurgitation problems, which are highly undesirable in malnourished infants that suffer from bad eating behavior. Therefore osmolality should be in the range of about 260 to about 450, preferably about 270 to about 370, and most preferably about 280 to about 340 mOsmol per liter product.

Usually, one or more vitamins are present. Preferably at least one vitamin selected from the group consisting of vitamin A, vitamin D, vitamin C, vitamin E, vitamin K and the vitamin B group are present. In particular, at least one compound from the vitamin B group selected from thiamine, riboflavine, niacine, vitamin B6, vitamin B12, biotin, folic acid, panthotenic acid is present. Vitamins may have various beneficial effects, such as described in the art. Further, it is thought that the presence of a vitamin may contribute to improving the Th1/Th2 ratio.

In a preferred product of the invention at least one organic acid is present that is capable of binding a free cation in aqueous solution, preferably capable of binding a free cation selected from copper ions and iron ions. Such organic acid may thereby have a stabilizing effect on a long chain polyunsaturated fatty acid. In particular thereby oxidation of the fatty acid may be reduced or even prevented.

Preferably at least one organic acid selected from citric acid and malic acid is present.

It is contemplated that an organic acid such as citric acid or malic acid helps to prevent sensitizing the subject to an allergen.

In addition one or more other food components may be present. In particular one or more components selected from the group consisting of choline and inositol may be present. Suitable concentrations are known in the art.

The invention further relates to a method for preparing a food product according to the invention, comprising:
  providing a amino acid fraction, a lipid fraction and optionally a non-digestible carbohydrate fraction, each comprising less than 0.01 wt. %, preferably less than 0.001 wt. %, based on the dry weight, peptide material having a molecular weight of more than 1000 D; and
  combining said fractions and optionally one or more other ingredients, thereby forming the product.

If one or more other ingredients are added, the content of peptide material having a molecular weight of more than 1000 should be such that it results in a product having less than 0.01 wt. % peptide material having a molecular weight of more than 1000.

Conventional raw materials for preparing a food product (lipid sources, carbohydrate sources, amino acid sources) are from a natural origin and typically contain peptides/proteins that can act as a T-cell epitope (typically having a molecular weight of over 1000 D). For instance, fish oil (as a source for AA and/or DPA) typically comprises peptide material.

In accordance with the invention care is taken that—in particular for the lipid fraction, the indigestible carbohydrate fraction (if present) and the amino acid fraction—raw materials are used in the final product that comprise no or only low amounts of such peptides and proteins. In particular, in combination they should result in less than 0.01 wt. % of peptidergic material having a molecular weight of more than 1000 D in the food product.

In principle providing a fraction having less than 0.01 wt. % (or even less than 0.001 wt. %) peptide material having a molecular weight of more than 1000 may be achieved in any way.

For instance, one may remove peptide material (including one or more enzymes that may be used in order to obtain the fraction) having a molecular weight of more than 1000 from a fraction in order to reduce the content to the appropriate concentration, e.g. by chromatography, precipitation and/or filtration, in particular micro and/or ultra filtration, to obtain a product having less than 0.01 wt %, preferably <0.001, more preferably <0.0001 wt % of this peptide material.

The skilled person will be able to find a suitable method.

One or more of the fractions may be provided by a process comprising lysis of bacteria and removing or hydrolysis of peptides (including proteins).

For instance, the non-digestible oligosaccharides may be obtained by acidic hydrolysis of a polysaccharide or enzymatic hydrolysis of a polysaccharide.

As a polysaccharide, one can, e.g., use a starting material that comprises more than 90% carbohydrate material and less than 1 wt % peptide material having MW>1000 dalton, e.g. by applying crystallization, denaturation, decomposition, separation, precipitation, or a combination thereof. This polysaccharide can than be treated with an enzyme and/or acid.

If needed, enzyme and other large proteins/peptides can subsequently be removed to achieve the desired purity.

Advantageously the non-digestible oligosaccharide is obtained by acidic hydrolysis. Thus the use of a potentially allergenic enzyme is avoided.

It is also possible to synthesize the non-digestible carbohydrate by (enzymatic) synthesis from smaller saccharides, in particular from monosaccharides, disaccharides and/or trisaccharides. Care should be taken that the enzyme does not remain in the product in too high a concentration.

A lipid fraction comprising free fatty acids, mono- and/or diglycerides may be obtained from triglycerides by acidic hydrolysis or enzymatic hydrolysis. In the latter case, the used enzyme(s) can be removed from the fraction by chromatography, for instance by dissolving the fraction in an apolar solvent and eluting the fraction over a polar column.

A suitable amino acid fraction may be obtained by hydrolysis or synthetically. An amino acid fraction is preferably made synthetically. A suitable way to provide a fraction synthetically is known in the art. If an enzyme is used, care should be taken that the enzyme is removed from the product.

The invention further relates to a method for decreasing the sensitivity of a subject to an allergen, comprising enterally administering a food product according to the invention to the subject, in particular an infant, more in particular an infant having an age of up to 10 years.

The invention further relates to a method for ameliorating an allergic reaction in a subject comprising enterally administering a food product according to the invention to the subject, in particular an infant, more in particular an infant having an age of up to 10 years.

The invention further may be used in the diagnosis of an allergy.

In particular a food product of the invention may be used in a method for diagnosing an allergy, comprising enterally administering a food product according to the invention to a subject, in particular an infant, more in particular an infant having an age of up to 10 years.

In such a method a subject showing an allergic reaction to a food, is provided with a food product of the invention as the sole nutrition within a sufficient time-span, typically of at least 2 hours from the moment of administration.

Care is taken that the subject is not exposed to non-food allergens.

During this period, the allergic reaction is monitored. If an existing allergic reaction disappears, it may be concluded that the food the subject had taken before caused the allergic reaction. If the allergic reaction is still pertaining it is most probable not the traditional food (taken before the food product of the invention was consumed) that caused the allergic reaction but an allergen of environmental origin.

The invention further relates to a lipid composition, in particular a lipid composition of natural origin, suitable as an ingredient in the manufacture of a non-allergenic food composition, comprising at least 80 wt. % based on the total weight of one or more lipids selected from the group consisting of triglycerides, diglycerides, mono-acylglycerides, phospholipids, lysophospholipids, ceramides, sphongosines, gangliosides, free fatty acids, salts of free fatty acids and esters of free fatty acids, said lipid composition comprising at least one of arachidonic acid and docosahexanoic acid, the lipid composition having a T-cell epitope content of less than 0.01 wt. %, based on the dry weight, preferably of less than 0.001 wt. %.

In particular, such fraction may be selected from phospholipide fractions, lysophospholipide fractions, ceramide fractions, enzymatically prepared diglyceride fractions and enzymatically prepared monoglyceride fractions.

Preferably, the lipid composition meets one or more features as identified above for the lipid fraction.

The invention further relates to an indigestible carbohydrate composition, preferably of natural origin, suitable as an ingredient in the manufacture of a non-allergenic food composition, comprising at least 80 wt. %, based on the weight of the carbohydrate fraction, of oligosaccharides having a degree of polymerization in the range of 3-20, the carbohydrate composition having a T-cell epitope content of less than 0.01 wt. %, based on the dry weight, preferably of less than 0.001 wt. %. Preferably, such composition meets one or more features as identified above for the carbohydrate fraction.

The invention further relates to a method for treating malnourishment in a patient suffering from celiac disease, cystic fibrosis, short bowel syndrome, inflammatory bowel disease, cystic fibrosis, epileptics or persons experiencing treatment with drugs, in particular non-steroidal anti-inflammatory drugs, chemotherapeutics, antimetabolics and antibiotics, which method comprises the administration of a food product according to the invention or an indigestible carbohydrate composition according to the invention wherein the product has an energy density of 2.5-3.3 kilojoule per milliliter or 10.0 to 13.2 kilojoule per gram dry weight.

The invention further relates to a method for reducing the risk of an anaphylactic shock due to administration of substances via parenteral route, comprising the administration of the food product according to the invention at least 1 hour prior to the moment of administration of said substance.

The invention further relates to a method for influencing the endogenous amounts of T helper cells and/or T regulatory cells, activating Toll-like receptors, or plasma levels of histamine or interferon-gamma comprising the administration of the food product according to the invention or a indigestible carbohydrate composition according to the invention.

The invention further relates to a method for treating or reducing the risk of occurring of diaper rash, hypersensitive skin reaction, disturbances of normal sleep behavior, excessive crying in an allergic infant or infant having an atopic constitution, comprising the administration of a food product according to the invention or an indigestible carbohydrate composition according to the invention.

EXAMPLES

Example 1

Non-Allergic Food Product Formulation

Non-allergic product that comprises per 100 ml (or 15.4 g powder)

| | | |
|---|---|---|
| Protein equivalents | 1.9 | g |
| Carbohydrates | 8.1 | g |
| Lipids | 3.5 | g |
| DHA | 17 | mg |
| AA | 20 | mg |
| LA | 0.6 | g |
| Alpha-LA | 60 | mg |
| Triglycerides | 3.4 | g |
| Diacylglycerides | 0.094 | g |
| Phospholipids | 30 | mg |
| Cholesterol | 30 | mg |
| Fiber | 0.6 | g |

Microingredients According to Regulations and Recommendations

In such a food composition fibers can be added from the following groups:
   a. Mixed oligosaccharides (DP2-20)
      Arabinoxylans
      Galactomannans
      Sialic acid OS
   b. uni-oligosaccharides 10-90
      mixed oligosaccharides 90-10
   c. uni-oligosacchrides 10-90
      mixed-oligosaccharides 90-10
      of which at least 50% comprises three monosaccharides Example 2

Nutritional Formulae for Epileptics of Young Age

Energy density: 0.6-0.77 kcal/ml or 2.52-3.24 kilojoule per milliliter Lipids: 5.5 to 7 g/100 ml ready to use formulae fatty acid profile:

palmitic acid: 15-40, preferably 22-38, most preferably 26-36 wt % of fatty acids and optionally but preferably one or more of: DHA: 0.16-8 wt %, AA: 0.4-8 wt %, AA/DHA=1-5:1 and LA (C18:2)/DHA=1-47:1 and wherein the lipid fraction optionally but preferably comprises more than 8 wt % of phospholipids, lysophospholipids, ceramides, sphingosides, glycolipids or cholesterol or equivalents thereof.

| Nutrition Information | Per 100 g Powder | Per 100 kcal* | Per 100 ml** |
|---|---|---|---|
| Energy kJ | 2918 | 413 | 292 |
| kcal | 707 | 100 | 70.7 |
| Protein g | 15.2 | 2.1 | 1.5 |
| Carbohydrate g | 7.6 | 1.1 | 0.76 |
| as sugars g | 0.68 | 0.1 | 0.07 |
| Optionally Fiber g | 1.0 | | |

| Typical Amino Acid Profile | g/100 g Powder |
|---|---|
| L-Alanine | 0.5 |
| L-Arginine | 0.53 |
| L-Aspartic Acid | 1.1 |
| L-Cystine | 0.42 |
| L-Glutamic Acid | 3.3 |
| Glycine | 0.29 |
| L-Histidine | 0.46 |
| L-Isoleucine | 0.75 |
| L-Leucine | 1.5 |
| L-Lysine1. | 2 |
| L-Methionine | 0.43 |
| L-Phenylalanine | 0.76 |
| L-Proline | 1.6 |
| L-Serine | 0.81 |
| L-Threonine | 0.73 |
| L-Tryptophan | 0.41 |
| L-Tyrosine | 0.81 |
| L-Valine | 0.99 |
| L-Carnitine | 0.03 |
| Taurine | 0.05 |

| Carbohydrate Profile | g/100 g Carbohydrate | g/100 g Powder |
|---|---|---|
| Dextrose | 1.9 | 0.14 |
| Lactose | 0.4 | 0.03 |
| Maltose | 6.7 | 0.51 |
| Maltotriose | 9.5 | 0.72 |
| Higher Saccharides | 81.5 | 6.2 |

| Vitamins | | Per 100 g Powder | Per 100 kcal* | Per 100 ml** |
|---|---|---|---|---|
| Vitamin A mg | RE | 781 | 110 | 78.1 |
| | IU | 2601 | 368 | 260 |
| Vitamin D mg | | 14.1 | 2 | 1.4 |
| | IU | 564 | 79.8 | 56.4 |
| Vitamin E mg a | T.E. | 8.9 | 1.3 | 0.89 |
| | IU | 13.3 | 1.9 | 1.3 |
| Vitamin C mg | | 134 | 19 | 13.4 |
| Vitamin K mg | | 29.8 | 4.2 | 3 |
| Thiamin mg | | 0.64 | 0.09 | 0.06 |
| Riboflavin mg | | 0.85 | 0.12 | 0.09 |
| Niacin mg | | 8 | 1.1 | 0.8 |
| Niacin equivalent (mg NE) | | 14.8 | 2.1 | 1.5 |
| Vitamin B6 mg | | 0.57 | 0.08 | 0.06 |
| Folic Acid mg | | 215 | 30.4 | 21.5 |
| Vitamin B12 mg | | 1.3 | 0.18 | 0.13 |
| Biotin mg | | 16.2 | 2.3 | 1.6 |
| Pantothenic Acid mg | | 5.8 | 0.82 | 0.58 |
| Choline mg | | 170 | 24 | 17 |
| Inositol mg | | 170 | 24 | 17 |

| Minerals | | Per 100 g Powder | Per 100 kcal* | Per 100 ml** |
|---|---|---|---|---|
| Sodium | mg | 318 | 45 | 31.8 |
| | mmol | 13.8 | 2 | 1.4 |
| Potassium | mg | 925 | 131 | 92.5 |
| | mmol | 23.7 | 3.4 | 2.4 |
| Chloride | mg | 547 | 77.4 | 54.7 |
| | mmol | 15.6 | 2.2 | 1.6 |
| Calcium mg | | 649 | 91.8 | 64.9 |
| Phosphorus mg | | 500 | 70.7 | 50 |
| Magnesium mg | | 81.7 | 11.6 | 8.2 |

| Trace Elements | Per 100 g Powder | Per 100 kcal* | Per 100 ml** |
|---|---|---|---|
| Iron mg | 10.7 | 1.5 | 1.1 |
| Copper mg | 710 | 100 | 71 |
| Zinc mg | 5.7 | 0.81 | 0.57 |
| Manganese mg | 0.92 | 0.13 | 0.09 |
| Iodine mg | 127 | 18 | 12.7 |

-continued

| | | | |
|---|---|---|---|
| Molybdenum mg | 31.8 | 4.5 | 3.2 |
| Selenium mg | 19 | 2.7 | 1.9 |
| Chromium mg | 31.8 | 4.5 | 3.2 |
| Fluoride mg | 0.85 | 0.12 | 0.09 |

Example 3

Typical Contents of a Lipid Fraction of a Product According to the Invention

Lipid fraction providing per 100 g fatty acids 0.7 g DHA and 0.7 g AA and comprising: per 95 g triglycerides:

| | |
|---|---|
| phospholipids | 0.5-4 g |
| cholesterol | 0.5-1.5 g and |
| glycolipids | 0.1-2 gram |

Example 4

Protein Fraction Suitable for Use in Anti-Allergic Formulae protein equivalent
synthetic amino acids
natural amino acids chosen from: Arg, Thr, Trp, Met, Ala, Trp, Cys, Leu, Ile, Val, Phe, Tyr in both D- or L-form.

Example 5

Anion Fraction as Present in Anti-Allergic Formulae According to the Invention

Per 100 ml ready to use formulae:

| | |
|---|---|
| Phosphate as P | 35 mg |
| Bicarbonate | 0.15 mg |
| Citrate | 0.4 mg |
| Orotate | 4 mg |
| Miscellaneous: chloride, | 92 mg |
| sulphate | 10 mg |

The invention claimed is:

1. A food product for ameliorating an allergic reaction in a subject by enterally administering the food product to the subject comprising:
   an amino acid fraction comprising at least one component selected from the group consisting of amino acids and peptides having a degree of polymerization of 7 or less; and
   a lipid fraction comprising at least one fatty acid selected from the group consisting of arachidonic acid and docosahexanoic acid,
   wherein the food product having a content of proteins and other peptides having a molecular weight of 1000 dalton or more being less than 0.01 wt. %, based on the total dry weight of the product, and wherein the amino acid fraction further comprising less than 0.01 wt. % of proteins and other peptides having a degree of polymerization of 8 or more, based on the total dry weight of the product.

2. The food product according to claim 1, further comprising a non-digestible carbohydrate fraction comprising at least 80 wt. %, based on the weight of the carbohydrate fraction, of oligosaccharides having a degree of polymerization in the range of 3-20, the oligomers comprising at least one or more moieties selected from the group consisting of fructose, galactose, glucuronic acid, galacturonic acids, xylose, mannose and arabinose moieties.

3. The food product according to claim 2, with the oligosaccharides comprising at least two different monosaccharide units selected from the group consisting of galactose, fructose, uronic acids, xylose, arabinose and mannose.

4. The food product according to claim 3, with the amino acid fraction comprising less than 0.001 wt. % of proteins and other peptides having a degree of polymerization of 8 or more.

5. The food product according to claim 2, with the amino acid fraction comprising less than 0.001 wt. % of proteins and other peptides having a degree of polymerization of 8 or more.

6. The food product according to claim 1, with at least 80 wt. % of the lipid fraction being provided by one or more lipids selected from the group consisting of triglycerides, diglycerides, mono-acylglycerides, phospholipids, lysophospholipids, ceramides, sphongosines, gangliosides, free fatty acids, salts of free fatty acids and esters of free fatty acids.

7. The food product according to claim 6, with the amino acid fraction comprising less than 0.001 wt. % of proteins and other peptides having a degree of polymerization of 8 or more.

8. The food product according to claim 1, with the amino acid fraction comprising less than 0.001 wt. % of proteins and other peptides having a degree of polymerization of 8 or more.

9. The food product according to claim 1, with the amino acid fraction providing about 1.0-6.9 g arginine, about 5.5-12 g threonine and about 2.2-6.0 g tryptophan per 100 g amino acids.

10. The food product according to claim 9, with the amino acid fraction comprising less than 0.001 wt. % of proteins and other peptides having a degree of polymerization of 8 or more.

11. The food product according to claim 1, comprising at least one mineral selected from the group consisting of iron and copper.

12. The food product according to claim 1, with the content of proteins and other peptides having a molecular weight of 1000 dalton or more being less than 0.001 wt. %.

13. The food product according to claim 1, with the content of proteins and other peptides having a molecular weight of 1000 dalton or more being less than 0.0001 wt %.

14. The food product according to claim 1, having a T-cell epitope content of less than 0.01 wt %.

15. The food product according to claim 1, wherein the amino acid fraction comprises all essential amino acids.

16. The food product according to claim 1, wherein the food product is intended for PKU patients and comprises all essential amino acids except for phenylalanine.

17. The food product according to claim 1, wherein the amino acid fraction consists of amino acids.

* * * * *